United States Patent [19]

Nam et al.

[11] Patent Number: 5,495,057

[45] Date of Patent: Feb. 27, 1996

[54] METHOD FOR THE PREPARATION OF DIFLUOROMETHANE

[75] Inventors: Kyung H. Nam; Doo C. Na; Dae S. Kim, all of Kyungnam, Rep. of Korea

[73] Assignee: Ulsan Chemical Co., Ltd., Kyungnam, Rep. of Korea

[21] Appl. No.: 398,965

[22] Filed: Mar. 2, 1995

[30] Foreign Application Priority Data

Dec. 28, 1994 [KR] Rep. of Korea ............... 38154

[51] Int. Cl.⁶ .................................... C07C 17/08
[52] U.S. Cl. .................................... 570/167
[58] Field of Search ............................ 570/167

[56] References Cited

U.S. PATENT DOCUMENTS 2,005,713  6/1935  Hoh ........................... 570/167
2,749,375  6/1956  Ruh et al. ..................... 570/167

*Primary Examiner*—Alan Siegel

[57] ABSTRACT

There is disclosed a method for the preparation of difluoromethane wherein methylene chloride is reacted with hydrogen fluoride in liquid phase, at a temperature of about 70° to 90° C. under a pressure of about 11 to 12 kg/cm².g in the presence of antimony pentachloride. It is important that the concentration of quinquevalent antimony is maintained at a level of 85% or more with the feed mole ratio of hydrogen fluoride to methylene chloride ranging from about 2.0 to 2.3.

Applicable to industrial scale, the method is operated in a batch system or in a continuous system. In addition, it exhibits superior conversion rate of the materials and production yield.

3 Claims, 1 Drawing Sheet

METHOD FOR THE PREPARATION OF DIFLUOROMETHANE

BACKGROUND OF THE INVENTION

1. Field of the Invention

The present invention relates, in general, to a method for the preparation of difluoromethane and, more particularly, to a method for reacting methylene chloride with hydrogen fluoride in liquid phase, applicable to industrial scale and superior in conversion rate of the materials and in production yield.

2. Description of the Invention

As compounds of chlorofluoro carbon (hereinafter referred to as "CFC") system which have extensively used for foaming agents, detergents, aerosol spraying agents, refrigerants and the like, are proved to be a main factor destructurizing the ozone layer of the stratosphere, there is increasingly demanded a substitute for CFC which less or little affects the ozone layer. In an effort to prevent the destruction of the ozone layer, hydrochlorofluoro carbon (hereinafter referred to as "HCFC") was developed. HCFC has an ozone depleting potential (hereinafter referred to as "ODP") of 0.02 to 0.1 which is somewhat lower than that of CFC. However, even though it is low in depleting ozone, HCFC still destructurizes the ozone layer. Owing to this, HCFC is destined to be prohibited from production and use in a few years, in accordance with protocol agreed internationally.

Accordingly, intensive research and study have been directed to development of substitutes that destructurize, by no means, the ozone layer, that is, have an ODP of zero as well as function equally to CFC. As a result of the research and study, a hydrofluoro carbon (hereinafter referred to as "HFC") system was developed. In the HFC system, there are known a variety of compounds, such as HFC-32, HFC-125 and HFC-134a. In the future, it is believed that HFC-32 is rapidly substituted for chlorodifluoro methane (hereinafter referred to as "HCFC-22") used at present, in a form of mixture refrigerant of HFC-32/HFC-134a (25/75 wt %) or HFC-32/HFC-125/HFC-134a (30/10/60 wt%), or in a form of azeotropic refrigerant of HFC-32/HFC-125 (60/40 wt%). The abbreviations HFC-134a and HFC-125 as used herein denote tetrafluoroethane ($CF_3CH_2F$) and pentafluoroethane ($CF_3CHF_2$), respectively.

HFC-32 may be prepared by two methods: gas phase method and liquid phase method. In the gas phase method, methylene chloride ($CH_2Cl_2$) and hydrogen fluoride (HF) are preheated and reacted with each other in gas phase, in the presence of a metal catalyst, such as Al or Cr-based catalyst well known to the art. On the other hand, the gas phase method, as implied by its name, is performed by reacting methylene chloride with hydrogen fluoride in liquid phase, in the presence of catalyst, but has not been adopted commercially, thus far.

The reaction processes for HFC-32 proceed sequentially and are as follows:

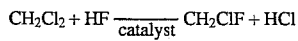

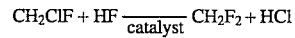

In the art, $CH_2ClF$ and $CH_2F_2$ are typically called HCFC-31 and HFC-32, respectively. As apparent from the above reaction formula, HCFC-31 is reclaimed in a reactor such that it reacts with HF, again, to produce HFC-32.

European Patent No. 0128510 suggests a preparation method for HFC-32 wherein methylene chloride and hydrogen fluoride are preheated and then, gaseous methylene chloride is reacted with gaseous hydrogen fluoride in the presence of a catalyst selected from a chrome-based compound, such as $Cr_2O_3$ and $CrF_3$, an aluminum-based compound, such as $Al_2O_3$, $AlCl_3$ and $AlF_3$, and the combinations thereof. In the case that a combination of the aluminum-based and the chrome-based compounds is employed as a catalyst, the aluminum-based compound is added in an amount of 0.1 to 50 parts by weight based on unit part of the chrome-based compound. The gas phase reaction of this European patent is carried out at a temperature of 200° to 450° C. under the atmosphere with the mole ratio of hydrogen fluoride to methylene chloride ranging from 1 to 20.

Japanese Patent Publication No. Sho. 58-100464 teaches that HFC-32 is prepared by vaporizing methylene chloride and hydrogen fluoride with heat and subjecting the resulting gaseous methylene chloride and gaseous hydrogen fluoride to gas phase reaction at a reaction temperature of 200° to 500° C. under atmosphere or pressure in the presence of a chrome catalyst, such as $CrF_3$, $CrCl_3$ and $Cr_2O_3$, with the mole ratio of gaseous methylene chloride to gaseous hydrogen chloride ranging from 1 to 20.

Supra patents describe preparation of HFC-32 with methylene chloride and hydrogen fluoride in the presence of a chrome-based or aluminum-based catalyst, requiring the catalyst to be molded into a pellet type with a dimension of 4 mmΦ×4 mmH or 4 mmΦ×6 mmH wherein Φ and H represent diameter and height, respectively. However, the molding of the catalyst is troublesome. In addition, the gas phase reaction is relatively complicated because it needs a preheater and a mass flow controller in order to vaporize liquid materials and to provide the gaseous materials in a constant rate. Further, since the gas phase reaction is executed at high temperatures, it is difficult to control the reaction temperature as compared with the liquid phase reaction. Furthermore, the high reaction temperature of the gas phase method not only makes reaction vessel corroded but also expedites ageing of the catalyst. Particularly, the methods suggested in supra patents exhibit low conversion rate of material (for example, conversion rate of methylene chloride is in a range of 76 to 85% and conversion rate of hydrogen fluoride 18 to 34% in the above-mentioned European patent, and conversion rate of methylene chloride 70 to 84% and conversion rate of hydrogen fluoride 25 to 31% in the Japanese patent mentioned), so that various economical countermeasures for the unreacted materials, such as separation of methylene chloride and hydrogen fluoride, recovery, purification and recycle, should be taken.

European Patent No. 0508660 discloses that HFC-32 is prepared by replacing the chlorine of HCFC-22 with hydrogen gas at a reaction temperature 135° to 140° C. in the presence of a catalyst in which a catalytically active material, such as palladium (Pd), platinum (Pt), nickel (Ni) and protoactinium (Pa), is incorporated into a carrier of active carbon in an amount of 0.5 to 20% by weight.

European Patent No. 0508631 employs a complex metal hydride catalyst, such as lithium aluminum hydride ($LiAlH_4$) and sodium brome hydride ($NaBH_4$). In this patent, the chlorine atom of HCFC-22 is substituted by hydrogen atom at a temperature of 20° to 71° C. in the presence of the complex metal hydride catalyst, to give HFC-32.

However, the two just mentioned patents are disadvantageous in that HCFC-22, primary converted from chloroform (CHCl$_3$), is used as a starting material. In addition, the conversion rate of HCFC-22 in the conventional methods is low, for example, on the order of 0.36 to 84.1%. Moreover, there is a serious problem of side reaction that byproducts, such as methane (CH$_4$), trifluoromethane (CF$_3$H), monochloromethane (CH$_3$Cl), ethane (CH$_3$CH$_3$), difluorodichloromethane (CF$_2$Cl$_2$) and trifluoromonochloromethane (CF$_3$Cl), are produced along with the object compound. Nowhere in the two supra patents is mentioned separation and purification of the by-products.

The above-described gas phase reaction methods for HFC-32 in which HF and CH$_2$Cl$_2$ are reacted at a temperature 200° to 500° C. in the presence of metallic catalyst (Al, Cr, Pa, Pt, Ni, etc.) with the mole ratio of HF to CH$_2$Cl$_2$ ranging from 1 to 20 and preferable 5 to 10 have a significant problem that the conversion rate of material is extremely low, for example 15–35% for HF and 70–85% for CH$_2$Cl$_2$. In turn, low conversion rate of HF and CH$_2$Cl$_2$ causes other problems. For example, it is difficult to recover the materials. In addition, the remaining materials along with the product and by-products form azeotropes, from which the product are hard to separate and purify. Consequently, the production yield is lowered.

The high reaction temperature in the gas phase reaction, 200° to 500° C. includes possible troubles that the reaction vessels might be corroded and by-products may be produced abundantly.

U.S. Pat. Nos. 2,749,374 and 2,749,375 introduce a liquid phase reaction for the preparation of HFC-32 with a catalyst of antimony halide. In the Examples of the patents, SbF$_3$ provided with Cl$_2$ or a combination of SbF$_3$ and SbCl$_5$ is utilized as the catalyst. As for reaction conditions, 2 to 3 moles of hydrofluoride per mole of methylene are provided at a temperature of 110° to 175° C. under a pressure of 400 Lb/cm$^2$.G. The catalyst is present in an amount of 0.2 to 2 moles per mole of methylene chloride, and Cl$_2$ is added in such a way to make the concentration of Sb$^{5+}$ at least 5%, with the aim of regenerating the catalyst.

However, this liquid phase reaction process has some problems. First, the catalyst is high in concentration (Sb:CH$_2$Cl$_2$=0.2–2:1) and rendered to be tar by the high reaction temperature. The tar catalyst may cause side-reaction. SbF$_3$, the catalyst, is difficulties for its preparation and provision. In addition, the reaction rate upon SbF$_3$ is slower than upon SbCl$_5$. Further, the conversion rates of the materials are low: 83–89% for methylene chloride; 70% for hydrochloride. What is still worse, the catalyst is very expensive and thus, not suitable for commercial production. It is believed that the prior techniques described in the supra U.S. patents are difficult to apply for industrialization, in consideration of the use of water cooled down 8° C. in a compressor, the high reaction temperature, and the batch system conducted in a laboratory scale.

SUMMARY OF THE INVENTION

An object of the present invention, therefore, is to overcome the above problems encountered in prior arts and to provide a novel method for the preparation of HFC-32 in a liquid phase reaction manner.

Another object of the present invention is to provide a novel method for the preparation of HFC-32 with a great production yield.

A further object of the present invention is to provide a novel method for the preparation of HFC-32, applicable to industrialization scale.

Based on the intensive research and study by the present inventors, the above object could be accomplished by a provision of a method for the preparation of HCF-32, comprising reacting methylene chloride with hydrogen fluoride in a liquid phase in the presence of SbCl$_5$ amounting to 0.18 to 0.43 mole of methylene chloride.

BRIEF DESCRIPTION OF THE DRAWINGS

The above objects and other advantages of the present invention will become more apparent by describing in detail the preferred embodiment of the present invention with reference to the attached drawings in which.

DETAILED DESCRIPTION OF THE INVENTION

Figure 1:
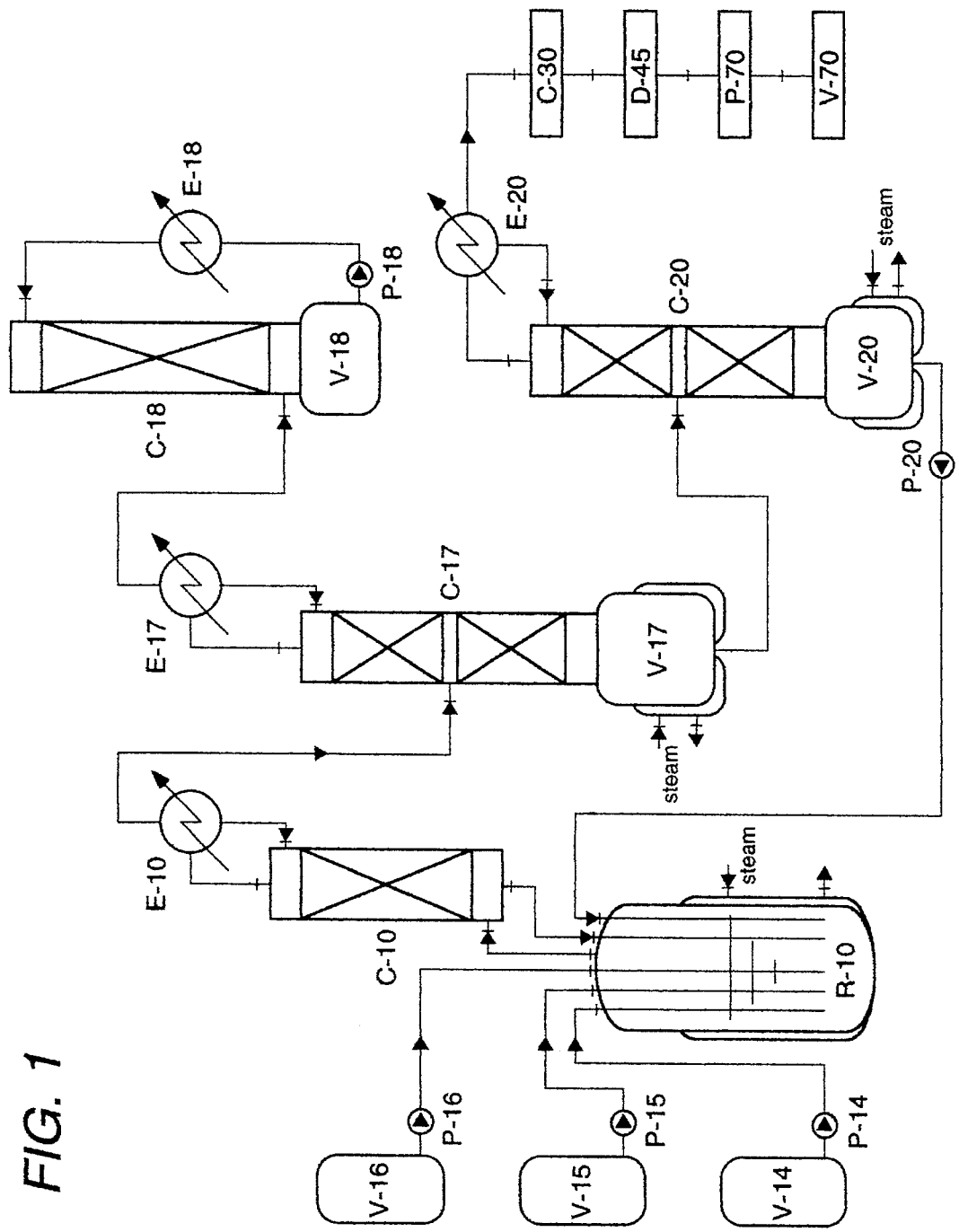
FIG. 1 is a diagrammatic view illustrating a procedure of the method according to the present invention.

In order to obtain HFC-32 in high conversion rate and production yield as well as in high reaction rate, there were conducted a number of experiments with various SbCl$_5$ concentration, reaction temperatures, and mole ratios of the materials. The experiments were carried out in a pilot plant rather than in a batch system of bench scale or laboratory equipments. Of course, bench scale test was undertaken with the aim of establishing an optimum reaction conditions.

Considering the fact that the amount of SbCl$_5$ is on the order of 0.3 to 0.4 mole per mole of material in the preparation process of CFC-11, CFC-12 and HCFC-22, the reaction experiment for HFC-32 was repeated with 0.05 to 0.43 mole of SbCl$_5$ per mole of methylene chloride. There was obtained a result that HFC-32 was prepared with high conversion rate of the materials (CH$_2$Cl$_2$ and HF) and high selectivity.

When the catalyst was fed in a small quantity, for example, 0.01 to 0.04 mole per mole of methylene chloride, the reaction rate was remarkably lowered in the reaction experiments. In addition, the conversion rate of the materials and the selectivity of HFC-32 were reduced.

Based on the results of the above bench scale tests, a continuous operation was conducted for a long time in a pilot plant with SbCl$_5$ amounting 0.18 to 0.43 mole per mole of methylene chloride. As a result, the conversion rate of the materials and the selectivity of HFC-32 are similar to those in the bench scale tests, but as the operation was continuously executed for a long time, it was expedited that the catalyst became tar and corrosion was effected in the reaction vessels.

By contrast, there were scarcely tar catalyst and corrosion of reactor vessel in the presence of 0.05 to 0.17 mole of SbCl$_5$ per mole of methylene chloride.

As above mentioned, the present invention was completed from a number of experiments conducted in a pilot plant wherein the mole ratio of SbCl$_5$ to CH$_2$Cl$_2$ was kept in a range of 0.05 to 0.17 with a variety of feed mole ratios of materials and the contact procedures between materials and reaction solvent. Based on the data obtained in the experiments, there is provided a method for the preparation of HFC-32, superior in conversion rate of material and production yield. In addition, the method according to the present invention can be applied for mass production of industrial scale.

Detailed reaction conditions of the present invention are as follows:

1. Methylene chloride and hydrofluoride which both of liquid phase are reacted with each other in the presence of antimony pentachloride ($SbCl_5$).
2. Pressure in the reaction system is maintained in a range of 11 to 12 $kg/cm^2$.g.
3. Reaction temperature is maintained in a range of 70° to 90° C.
4. The feed mole ratio of $HF/CH_2Cl_2$ is on the order of 2.0 to 2.3.
5. The catalyst is added in an amount of 0.05 to 0.17 mole per mole of methylene chloride.

According to the present invention, conversion rate of methylene chloride and hydrogen fluoride can be raised up to 91% and 82%, respectively, by control of the reaction conditions, such as the mole ratio of materials (HF, $CH_2Cl_2$), reaction temperature and pressure under the condition that the concentration of $Sb^{5+}$ is maintained at 85% or more. In addition, since the liquid phase reaction of the present invention can be driven with low catalyst concentration (mole ratio of $SbCl_5$ to $CH_2F_2$ 0.05–0.17:1), not only is the catalyst protected from being tar, but also the side reaction is prevented from occurring. Further, the above reaction conditions are able to afford to be free in selecting reaction vessels, and stainless steel are enough for the material for the reaction vessels of the present invention.

As previously mentioned, the catalysts of the conventional gas phase reaction are easily aged and thus, have short life span due to high reaction temperatures. What is still worse, they are very expensive and difficult to purchase. On the contrary, the catalyst of the present invention is used in liquid phase and thus, has a semipermanent life span. Further, it is economically advantageous in that it is cheap and easy to purchase.

The reaction for HCF-32 according to the present invention may be carried out in a typical apparatus. First, the materials (HF and $CH_2Cl_2$) and the catalyst ($SbCl_5$) are charged into a temperature-controllable reactor and reacted with each other therein. This reactor equipped with a reflux column and a reflux condenser which prevent powder-flight of the catalyst in an air stream generated from the reactor as well as reflux unreacted materials to improve the conversion rate of the materials.

The preferred embodiments of the present invention will now be further described in the following examples with reference to the accompanying drawing.

EXAMPLE

Into a 450 L stainless reactor R-10 (24B×1500 mm) equipped with a reflux column (8B×5200 mm) and a reflux condenser (10B×1900 mm, 6.25 $m^2$), methylene chloride ($CH_2Cl_2$) was charged from a methylene chloride reservoir V-16, and antimony pentachloride ($SbCl_5$) was added in amounts given as listed in the following Table 1.

The reactor was slowly heated to a temperature of 70° to 90° C., and then, liquid hydrogen fluoride (HF) was charged from a hydrogen fluoride reservoir V-15 into the reactor R-10, to subject the catalyst to fluorination. At the moment, hydrogen fluoride and methylene chloride were provided so continuously as to maintain the mole ratio of HF to $CH_2Cl_2$ in a range of 2.0 to 2.3 with the reactor being under a pressure of 11 to 12 $kg/cm^2$.g.

As the reaction proceeded, chlorine ($Cl_2$) was intermittently injected from a chlorine reservoir V-14 into the reaction system in order to prevent the activity of the catalyst from being lowered. In the catalyst, the concentration of quinquevalent antimony ($Sb^{5+}$) should be kept in a range of at least 85%.

A first packed column C-10 and a first condenser E-10 of the reactor R-10 served to improve the selectivity of HFC-32 by condensing and refluxing unreacted materials.

Mixed gases resulting from the reaction were passed into a second packed column C-17, wherein hydrogen chloride gas was separated. Then, the separated hydrogen chloride gas went into a second packed column E-17 and drained from the top thereof into a third packed column C-18 wherein it was absorbed in water to produce a 35% hydrochloric acid solution which was in turn stored in a hydrochloric acid reservoir V-18-18.

In the meanwhile, crude products effluent from a reboiler V-17 was passed into a fourth packed column C-20 wherein they were separated. At the moment, HCFC-31, which is high in boiling point, and a small quantity of HF and $CH_2Cl_2$ were recycled into the reactor R-10 while the object product, which is low in boiling point, was sequentially subjected to alkaline wash (C-30), dry (D-45) and pressurization (P-70) and then, stored in a product reservoir V-70.

During the reaction, a refrigerant of −15° to −20° C. was charged into a material condenser E-10 and a product condenser E-20, whereas a refrigerant of −30° to −32° C. and a cooling water of 20° to 25° C. were charged into the hydrogen chloride condenser E-17 and a heat exchanger E-18.

The conversion rates of material were measured and the results are given as shown in the following Table 1, along with gas chromatography analysis results.

TABLE 1

| | Reaction Condition | | Composition of | | Conversion Rate | |
|---|---|---|---|---|---|---|
| | $SbCl_5$ Conc. | Mole Ratio | | | | |
| Exam. | ($SbCl_5/CH_2Cl_2$ | Of Material | Product Gases | | $CH_2Cl_2$ | HF |
| No. | Mole Ratio) | ($HF/CH_2Cl_2$) | HCFC-31 | HFC-32 | (Wt %) | (Wt %) |
| 1 | 0.05/1 | 2.3/1 | 13.65 | 86.35 | 91.7 | 82.65 |
| 2 | 0.07/1 | 2.3/1 | 10.87 | 89.13 | 92.5 | 85.26 |
| 3 | 0.17/1 | 2.0/1 | 6.48 | 93.52 | 93.6 | 86.92 |

In Example 1, 100 kg of methylene chloride was charged into the reactor, along with 17.60 kg of the active catalyst ($SbCl_5$), whereas, in Example 2, along with 24.63 kg of the active catalyst and, in Example 3, along with 59.85 kg.

Other features, advantages and embodiments of the invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

What is claimed is:

1. A method for the preparation of difluoromethane, wherein methylene chloride is reacted with hydrogen fluoride in liquid phase at a temperature of from 70° to 90° C. and in the presence of a catalyst of antimony pentachloride ($SbCl_5$) with the mole ratio of the catalyst to methylene chloride ranging from 0.05 to 0.17.

2. A method in accordance within claim 1, wherein said catalyst has a concentration of pentavalent antimony ($Sb^{5+}$) maintained at a level of 85% or more.

3. A method in accordance within claim 1, wherein the reaction is conducted at a pressure of 11 to 12 kg/cm².g.

* * * * *